US010231681B2

(12) United States Patent
Bruno et al.

(10) Patent No.: US 10,231,681 B2
(45) Date of Patent: Mar. 19, 2019

(54) METHOD AND APPARATUS FOR ADJUSTING TECHNICAL EXPOSURE FACTORS DURING RADIOGRAPHIC ACQUISITION

(71) Applicants: Andrea Bruno, Imola (IT); Gianluca Manuzzato, Imola (IT); Giacomo Zoccatelli, Negrar (IT)

(72) Inventors: Andrea Bruno, Imola (IT); Gianluca Manuzzato, Imola (IT); Giacomo Zoccatelli, Negrar (IT)

(73) Assignee: CEFLA SOCIETÁ COOPERATIVA, Imola (BO) (IT)

( * ) Notice: Subject to any disclaimer, the term of this patent is extended or adjusted under 35 U.S.C. 154(b) by 792 days.

(21) Appl. No.: 14/557,497

(22) Filed: Dec. 2, 2014

(65) Prior Publication Data

US 2015/0190102 A1    Jul. 9, 2015

(30) Foreign Application Priority Data

Dec. 2, 2013    (IT) .............................. BO2013A0669
Dec. 2, 2013    (IT) .............................. BO2013A0670

(51) Int. Cl.
*A61B 6/00*    (2006.01)
*A61B 6/14*    (2006.01)

(52) U.S. Cl.
CPC ................ *A61B 6/14* (2013.01); *A61B 6/488* (2013.01); *A61B 6/542* (2013.01); *A61B 6/4441* (2013.01)

(58) Field of Classification Search
CPC ................................. A61B 6/488; A61B 6/542
See application file for complete search history.

(56) References Cited

U.S. PATENT DOCUMENTS 5,124,913 A    6/1992    Sezan
5,995,583 A    11/1999    Schick
(Continued)

FOREIGN PATENT DOCUMENTS

DE    102010042761    4/2012
EP    2574280    4/2013
EP    2614773    7/2013

OTHER PUBLICATIONS

Elbakri Idris et al.: "Automatic exposure control for a slot scanning full field digital mammography system," Mdical Physics, AIP, Melville, NY, US, vol. 32, No. 9, Aug. 22, 2005, pp. 2763-2770: Abstract, Figs. 1-5, Section "Materials and Methods".

*Primary Examiner* — Dani Fox
(74) *Attorney, Agent, or Firm* — Themis Law

(57) ABSTRACT

A method and apparatus for acquiring a radiographic image of a patient includes using an X-ray source and at least a X-ray detector supported in opposed positions, the area under investigation being positioned between the X-ray source and detector in the propagation bundle of the radiation emitted by the X-ray source, the X-ray source and detector being movable along a pre-set trajectory due to at least two movements. The X-ray dose administered to a patient can be adjusted automatically, dispensing the minimum dose necessary to achieve a radiographic image of good quality. The method and apparatus provide for performing a scout acquisition, preceding the acquisition of a real panoramic image, in a particularly efficient way. During the scout acquisition, data are collected for adjusting the X-ray dose for the following radiographic image acquisition.

12 Claims, 10 Drawing Sheets

(56) References Cited

U.S. PATENT DOCUMENTS

| | | |
|---|---|---|
| 6,377,656 B1 * | 4/2002 | Ueki .................... A61B 6/4225 378/98.7 |
| 7,787,586 B2 | 8/2010 | Yoshimura |
| 2007/0058772 A1 | 3/2007 | Schutz |
| 2009/0168966 A1 | 7/2009 | Suzuki |

* cited by examiner

RESET

SCOUT

EXAM START

EXAM

RESET

SCOUT

EXAM START

EXAM

METHOD AND APPARATUS FOR ADJUSTING TECHNICAL EXPOSURE FACTORS DURING RADIOGRAPHIC ACQUISITION

FIELD OF THE INVENTION

The present invention relates to the technical field of dental digital radiographic apparatuses that are known as panoramic apparatuses. In particular, the invention relates to a method and an apparatus for patient specific, real time automatic adjustment of the X-ray dose administered to a patient, so as to dispense the minimum necessary dose to produce a radiographic image of good quality.

BACKGROUND OF THE INVENTION

These types of apparatus produce a panoramic image of the dental arches of a patient, exposing the skull of a patient to X-rays. Panoramic radiography (also known as orthopantomography) produces a radiographic image of a curved plane, also known as Welander curve, approximating patient jaws, with blurring of the anatomical structures laying outside a narrow layer around the predesigned curved plane. The set of movements that mechanical parts must perform to achieve this result is called trajectory. This technology has been known since the 1950s. For the first 30-40 years (1950-1990), a film used to be exposed to X-rays. Today these types of apparatus use digital sensors, converting the X-ray impinging on the X-ray detector into an electric signal, which, suitably processed, forms a digital image.

The X-ray bundle undergoes attenuation while passing through different tissues of the patient; this attenuation determines the degree of exposure of a radiographic image. Different tissues attenuate X-rays in different ways according to their density, and this allows distinguishing a tissue from another. The correct exposure is obtained by balancing the intensity of X-ray bundle, so that the tissues of clinical interest become well visible and detailed. With an excessive exposure, tissues of low-medium density are crossed by X-rays without an attenuation that can detected (overexposure), while an exposure that is too low entails an excessive X-ray attenuation by more dense tissues, so that they cannot be distinguished from the neighboring tissues (underexposure).

In case of overexposure or underexposure, a re-take may be necessary. One must always keep into account that X-rays can lead to patient biological damage, as X-rays are ionizing radiations which can damage cell DNA. Therefore, the need to administer the lowest X-ray dose for the individual patient under examination is apparent.

Typically, a panoramic apparatus comprises an X-ray source and detector fixed to the ends of a rigid support, which turns around the patient. It also comprises a patient positioning and immobilizing device, which holds the patient in position during the acquisition.

Technical parameters that influence the intensity of the X-rays emitted from the source are:
X-ray tube power (kV),
X-ray tube current (mA),
duration of exposure (sec), and
film speed.

Originally, in film analog apparatuses, this last parameter used to determine how long a portion of the film was exposed to radiation, and film direction. This parameter in many of today's digital apparatuses was maintained as term, and corresponds to the speed and reading direction of X-ray sensor; elsewhere it is replaced by a parameter called clock TDI. In both cases, its effect on the quality of image exposure is similar.

The exposure for a patient can be adjusted by a professional operator, who can evaluate in advance the right X-ray dose needed for a good radiographic image, on the basis of his/her professional competence. Many manufacturers propose to operator pre-defined settings of these parameters, suitably set according to patient's gender and size, e.g. distinguishing among child, woman, man, and small, medium large size; such a system is described e.g. in U.S. Pat. No. 4,618,974 (Siemens). Anyway, the selection of these settings is always left to human operator.

Over the years, automatic adjusting devices were developed, which set the exposure according to a suitably chosen criterion (best contrast, lowest dose, etc.). These devices are known as AEC (Automatic Exposure Control) devices. The solutions nowadays available on the market can be subdivided into two categories:

parameters adjustment according to a pre-acquisition exposure (also known as scout);

continuous parameters adjustment during the acquisition (also known as run-time AEC).

A first way of the known art to solve the present technical problem consists in devices based on measuring, through dosimeters or similar devices, X-ray attenuation during scout acquisition. These detectors can be placed in one or more areas on the detector side (wither a sensor or a film), and can be fixed, mobile or removable. Such technique is described e.g. in patents U.S. Pat. No. 4,813,060 (Siemens), U.S. Pat. No. 5,425,065 (Instrumentarium) and EP 0574368 (Orion Yhtymae Oy). The detectors provide a direct measurement of X-ray attenuation through patient's tissues.

The disadvantages of this kind of solution are due to the need of specific mechanisms for dosimeter reading, their maintenance, the managing of their volume and the optimization of a work flow, wherein the attenuation measuring step and the following exposure to obtain images need supports, interfaces and data processing different from each other. When digital detectors replaced films, digital detectors replaced the use of specific dose detectors, since digital detectors can be used both for attenuation measuring during pre-acquisition and for image formation during the acquisition. The use of the same type of detector removes the need of correlating different signals (provided from a dosimeter and a digital detector) to exposure, preventing the need of cross-calibrations and cross-checks between the two systems.

Many of these mechanisms, though, do not take into account patient's structure and anatomical peculiarities, or the human operator must choose suitable exposure parameters according to his/her professional experience and competence, looking at scout image. In this case the time needed for the acquisition becomes longer, and a wide scout or more than one scout is required to detect the anatomical portion of interest. Moreover, the use of a scout requires the administration of a further (small) X-ray dose to patient.

If scout image is too small, or parameter computing algorithm is not specific for the acquired anatomic portion, or operator's intervention is not required in choosing parameters, the automatic setting of emission can become very sensitive to patient's positioning or peculiar bone structure.

A second way of known art for solving the present technical problem is a continuous time adjustment of exposure during the acquisition; the most popular methods require complex feed-back control mechanisms of X-ray tube. Such a technique is described e.g. in patent U.S. Pat.

No. 4,333,012 (Morita). According to this solution, a control system must be designed, which, during the acquisition, reads at time t the content of detector, processes it to get suitable emission parameters and adjusts the emission at time t+1 according to them. This entails designing X-ray tubes modulating their emission in very short time, with a very stable answer to input parameters and very short transient state, and a very fast system of detector reading and analysis.

In addition to technical complexity and high cost of this solution, one of its main disadvantages is that in situations of peculiar irregularity of patient's anatomy, or in the presence of metallic prostheses, or of a material much denser than adjoining tissues, the value of parameters computed at time t can be not suitable at the following time.

Using this technique, the image obtained risks to become a puzzle of portions of tissue exposed in very different way during the same acquisition, making comparative analyses very difficult between tissues having similar features, but positioned in points far away from each other, as e.g. in the case of bone density between right and left mandibular condyle.

A third way of solving the present technical problem consists in devices for measuring patient's dimensions of skull and size (e.g. height and skull diameter) based on an alleged correlation between these external measures and bone tissues thickness and density. One method of this kind is described in patent EP 1161122 (Palodex). Such correlation is purely statistical and does not take into any account the anatomical, pathological or personal peculiarities of the patient (e.g. osteoporosis, bone age, etc.).

According to a further aspect, the present invention relates to dental radiographic apparatuses, known as panoramic apparatuses and in particular to a method and an apparatus capable of performing a scout acquisition, preceding the acquisition of a real panoramic image, in a particularly efficient way.

This additional aspect can be independent or combined with the above illustrated additional aspects.

Typically, a panoramic apparatus comprises an X-ray source and detector fixed to the ends of a rigid support, while the patient is positioned in an intermediate position between the X-ray source and detector.

In the known art, apparatuses are known wherein the X-ray source and detector are moved according to pre-set trajectories due to the combination of three movements, i.e. a rotational movement around an axis of rotation of the rigid support due to which X-ray source and detector are moved along a circular trajectory around said axis and around the patient, and a translational movement of the axis of rotation of support arm according at least one or two different directions in the horizontal plane perpendicular to the axis of rotation of the support arm. Moreover, apparatuses are also known, in which the displacement according to two directions in the plane perpendicular to the axis of rotation of the support arm occurs not in a translational way but in a rotational way, due to an angular transfer of the axis of rotation of the support arm around an axis of rotation parallel to the axis of rotation of the support arm, as described e.g. in WO 2011064449A1 (Planmeca).

A panoramic apparatus also comprises a patient positioning and immobilizing device for holding the patient during the acquisition.

In the known art, in the normal working flow a human operator must perform some manual operations for setting the apparatus in order to achieve an image of good quality. Such operations comprise patient positioning and the choice of technical exposure factors, up to the setting of additional options provided by the apparatus, in order to obtain a trajectory of X-ray source and detector of the panoramic apparatus during the following acquisition as accurate as possible of the single patient's Welander curve.

Nowadays, the majority of manual operations are left to the operator's experience and competence. Many apparatuses have devices helping the operator in performing manual operations: e.g. the apparatus proposes to the operator pre-defined settings of technical exposure factors, suitably adjusted according to the patient's gender and size. Such a system is described e.g. in U.S. Pat. No. 4,618,974 (Siemens). However, the selection of those settings is always left to a human operator. The system described in U.S. Pat. No. 4,618,974 is based on statistical criteria and on operator competence.

Technical exposure factors (X-ray tube power (kV), X-ray tube current (mA), duration of exposure (sec) and film speed) and/or acquisition trajectory may be adjusted more precisely by performing a pre-acquisition of the single patient, known in the art as a scout image.

Different kinds of scout image are known in the art. A first kind acquires the entire area of interest, from which the operator then extracts a Region Of Interest (ROI). Based on ROI, technical exposure factors are then set. A second kind consists in acquiring a scout having reduced dimensions with respect to the area of interest, assuming that this small area is representative of the total area of interest, as described e.g. in U.S. Pat. No. 7,519,155 (Morita).

Another way in the known art consists in acquiring a patient's image in the visible range, to then adjust panoramic trajectory to the anatomy of that specific patient (face scan). A patent describing the use of a camera connected to a panoramic apparatus is e.g. U.S. Pat. No. 6,081,739 (Lemchen).

The evolution of the known art is going toward making the adjustment of technical exposure factors and/or acquisition trajectory more and more automatic and operator-independent. Therefore, methods and devices automatically obtaining the necessary information from the scout image are being designed.

For the success of automatisms and for better patient comfort, the time interval between scout acquisition and panoramic real acquisition should be as short as possible, in order to prevent patient movement between scout and real panoramic acquisition.

Two different problems may occur due patient movement:

In a first case, the patient moves during real panoramic acquisition, producing motion artifacts.

In a second case, the patient stands still during scout acquisition and real panoramic acquisition, but moves between scout acquisition and real panoramic acquisition, invalidating the assumption that the scout is representative of the area to be acquired during the real panoramic acquisition.

In the second case, an operator needs to obtain a scout of a broader area, administering a higher X-ray dose to the patient. The operator must always to keep into account that X-rays can lead to patient biological damage, as X-rays are ionizing radiations which can damage cell DNA. Therefore, the need is apparent to administer the lowest possible X-ray dose to a patient under examination.

SUMMARY OF THE INVENTION

An object of the present invention is solving the technical problem consisting in the adjustment of technical exposure parameters with an automatic adjustment method, free of the above-described problems, which can lead to a diagnostically valid panoramic image.

This object is achieved by a method and an apparatus having the features described hereinafter.

The proposed mechanism is based on the acquisition of a pre-acquisition scout of a well defined anatomic portion of the patient, with a simple algorithm for computing the optimal exposure for a given patient.

The present invention provides the advantage that, without a specific hardware structure, the attenuation measures performed on the scout provide reliable values of X-ray attenuation caused by patient tissues and are directly correlated to the exposure degree of the image obtained with the following acquisition.

Another advantage is that the present invention does not require parameter modulation during acquisition, ensuring constancy of exposure for the entire duration of the acquisition and its repeatability.

Additional advantages are that the present system is operator-independent, does not require additional elements with respect to the components needed to obtain the image, is of easy realization without requiring control and process devices over those needed for standard use.

Another aim of the present invention consists in performing a pre-acquisition imaging known as scout, such as that operator intervention is kept to a minimum, the area acquired during scout acquisition is as small as possible, and the acquisition of both scout image and real image is performed in a time as short as possible and with optimal comfort for operator and patient.

This object is achieved by a method and an apparatus as described hereinafter.

In the present invention, a method and an apparatus are described wherein a scout acquisition of a single patient is performed immediately before real panoramic acquisition. Such scout typically has a much smaller dimension (1-8%) than the area acquired during real panoramic acquisition. For acquiring the scout image, apparatus movement possibilities are exploited, in that scout acquisition occurs with a rotation direction of X-ray source and detector around the patient which is opposed to that of the real panoramic acquisition.

It is to be noted that there is a relation between acquisition time and dimension of the acquired area. As a matter of fact, considering a substantially constant speed of rotation of the X-ray source and detector around the virtual rotation center (CVR), the temporal duration of the acquisition corresponds to a given angular displacement of X-ray source and detector around the patient, and therefore to a given dimension of the acquired area.

A first advantage of the present invention is that there are no additional steps for both operator and patient in the acquisition flow over the known art.

A second advantage of the present invention is minimizing the overall time for acquiring a panoramic image.

A third advantage of the present invention is minimizing the probability of patient motion between scout acquisition and real panoramic acquisition.

A fourth advantage of the present invention is minimizing and tailoring the X-ray dose administered to the single patient undergoing examination.

In the present specification and in the claims, the term "virtual rotation center" (CVR) has the same meaning of instant center of rotation in cinematic or also of instantaneous center of zero velocity (IC). Considering a rigid body experiencing a general plane motion (in two dimensions), the instant center is an imaginary point lying on an imaginary axis of zero velocity, about which a rigid body appears to rotate at a given instant and which axis is always perpendicular to the plane of motion. The instant center is a limiting case of the so-called pole of planar rotation, which is the point around which any planar displacement of a body considered as a combination of a planar rotation and of a planar translation can be viewed as a rotation around this pole. If the initial and end position of the body are separated by an instant of time in a planar movement, then the pole of displacement becomes an instant center of rotation.

In the particular motion of the x-ray source and of the detector, the arm carrying the X-ray source and the detector is displaced by a roto-translational movement to displace the source and the detector along non-circular paths (Welander curve). Thus the instant center of rotation changes its position in space for different segments of said path for the source and the detector. The path of the instant center of rotation in time is called centrode.

BRIEF DESCRIPTION OF THE DRAWINGS

Further advantages and properties of the present invention are disclosed in the following description, in which exemplary embodiments of the present invention are explained in detail based on the drawings:

FIGS. 7A-7D: Movement steps of the rotating arm supporting X-ray source and detector during the acquisition of an overall scout+panoramic image according to the present invention, wherein FIG. 7A depicts the rotating arm at reset position, FIG. 7B depicts the rotating arm at scout position, FIG. 7C depicts the rotating arm at exam start position, and FIG. 7D depicts the rotating arm at exam position;

FIGS. 8A-8B: Movements of said rotating arm in a full-frame acquisition system, wherein FIG. 8A depicts a small portion of an acquisition and FIG. 8B depicts a small portion of an acquisition with inverted direction of detector reading;

DETAILED DESCRIPTION OF EMBODIMENTS OF THE INVENTION

Figure 1:
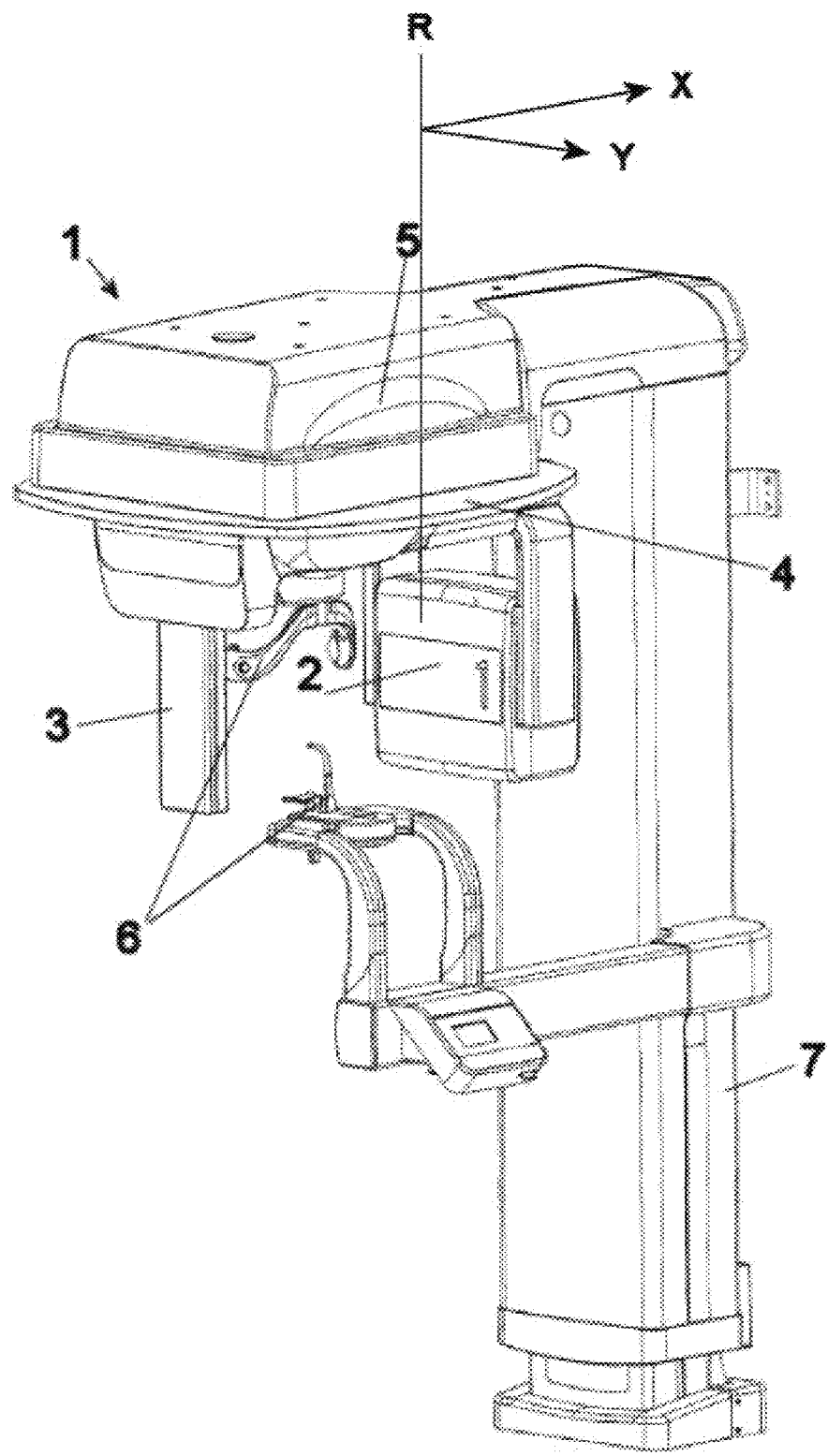
FIG. 1: Exemplary panoramic radiographic apparatus.

FIG. 1 shows a typical panoramic radiographic apparatus 1, comprising an X-ray source 2 projecting a collimated X-ray bundle across a patient (not shown), a bi-dimensional X-ray detector 3 positioned to measure the intensity of radiation after it has crossed the patient, a C-arm 4 on which said X-ray source 2 and detector 3 are fixed at opposed ends, a mechanical system 5 rotating and translating said support around the patient, in order to acquire radiographic images from different positions; and an electronic system (not shown) to control and synchronize the working of the various apparatus components. Panoramic apparatus 1 comprises moreover a device 6 for positioning the patient, in FIG. 1 consisting of a bite and supports for positioning the patient's skull. The position of C-arm 4 can be adjusted according to patient height due to vertically mobile post 7.

Figure 2:
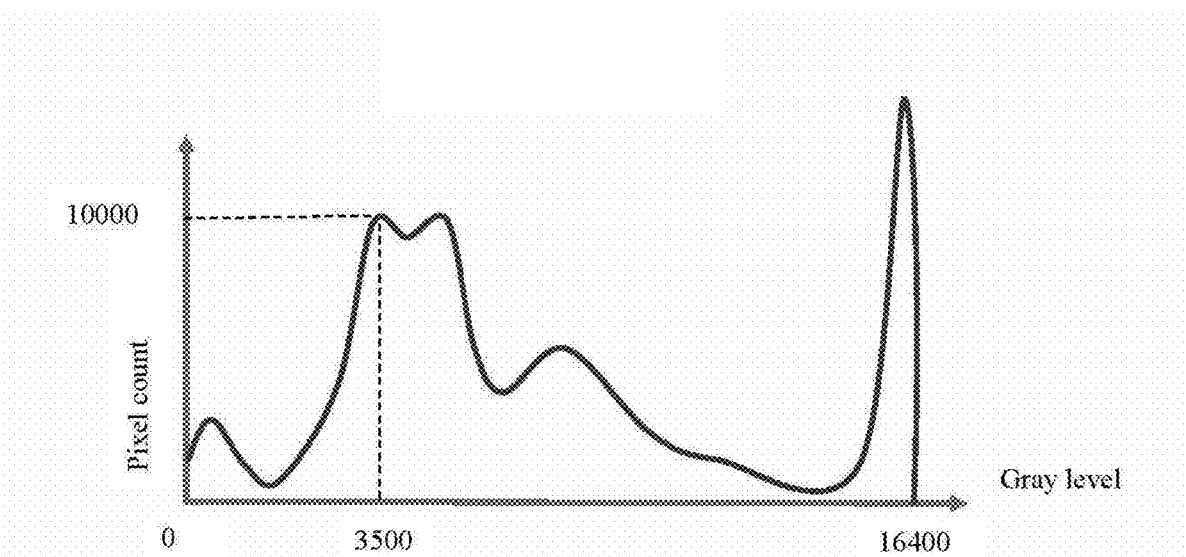
FIG. 2: Histogram of grey levels of a typical panoramic radiographic image.

FIG. 2 shows a histogram of grey levels of a typical panoramic radiographic image. The tissues crossed by X-rays attenuate X-rays in a way proportional to the atomic density of the tissue. As a consequence, given an input X-ray radiation, the denser tissue will absorb a higher quantity of radiation with respect to the less dense tissue. Therefore, in the first case a lesser quantity of X-ray radiation will impinge on the X-ray sensor with respect to less dense tissue. In practice, a black-and-white image will be obtained, ranging from pure white to pure black, passing through a gradation of intermediate grey's. The number of intermediate grey levels depends on the quality of the acquisition system. Typically, present day digital acquisition system are designed with 16 bits and therefore can show $2^{16}$ grey levels.

Any digital radiographic image consists of a pixel matrix, each of which has a grey level determined by the quantity of X-rays attenuated by the passage through the patient's tissues corresponding to the image pixels. Starting from grey levels, other kinds of more or less complex attenuation measure, such as e.g. Hounsfield Unit (HU), or conversion of grey scale to a polychromatic scale, can be derived. A method according to the present invention can anyway be analogously applied to all cases, in which the image is codified as a set of small units, each characterized by one or more values describing radio opacity. A person of skill in the art can use and combine the features of this invention in any different way that technology and knowledge allow. In general, for each radiographic image a histogram like that of FIG. 2 can be represented, bearing grey levels on an X-axis and the number of pixels having that grey level on a Y-axis.

In the exemplary histogram shown in FIG. 2, 10,000 pixels with a grey level of 3,500 are present. The histogram of the image is a way to show the quality of the radiographic image. If the pixels were present only in a fraction of grey levels, an image having insufficient contrast would result, where distinguishing among the different kinds of tissue would be difficult. Vice versa, a histogram showing a wide distribution of grey levels corresponds to a radiographic image where different grey levels are assigned to the different kinds of tissue, and, therefore, tissues are easily distinguishable from each other.

Figure 3:
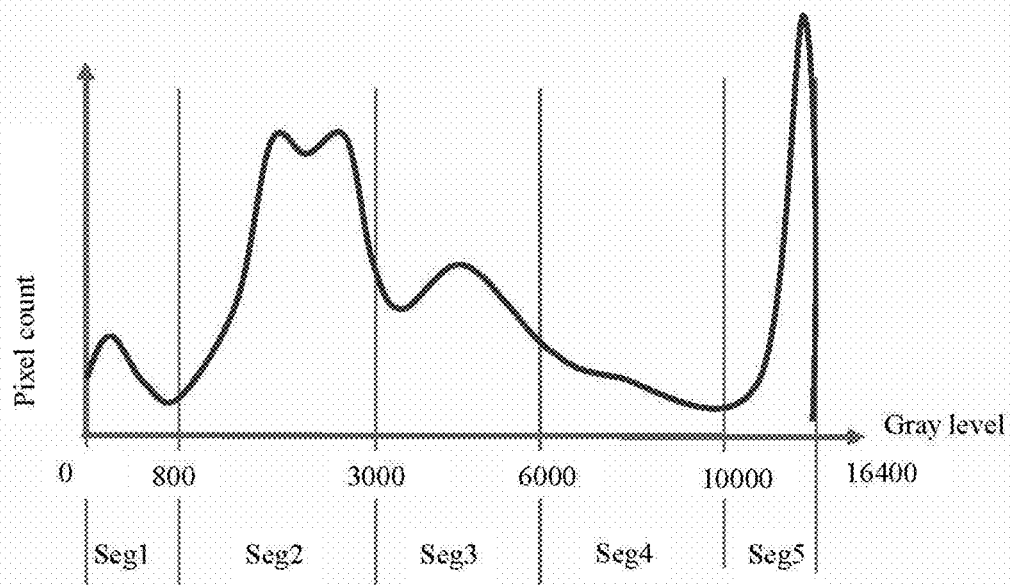
FIG. 3: Histogram of grey levels of a radiographic image to perform the method of the present invention.

In FIG. 3 a histogram prepared for use in a method according to the present invention is shown.

The grey levels (0 to 16,400) in the present example are subdivided into five sectors, each corresponding to the grey levels of a tissue typically represented in a panoramic image. For example, the values attributable to each sector of FIG. 3, assuming that the intensity of grey levels is a way to represent the radio-opacity of tissues, are:

Sector 1 [0-800]: metal and prosthesis
Sector 2 [800-3000]: hard bone
Sector 3 [3000-6000]: spongy bone
Sector 4 [6000-10000]: soft tissues
Sector 5 [10000-16400]: airways.

The ends identifying a sector can be both fixed (static segmentation) and variable (dynamic segmentation). For example, the segmentation can be correlated to particular trend lines of the histogram, or to minimum/maximum of a polynomial approximation of the histogram, etc.

The same sectors can have overlapping regions and not necessarily be adjoining to each other. The known types of mathematical/numerical analysis to achieve histogram segmentation can be different and of different complexity. In the present embodiment a static segmentation in sectors without overlapping was chosen.

Figure 4:
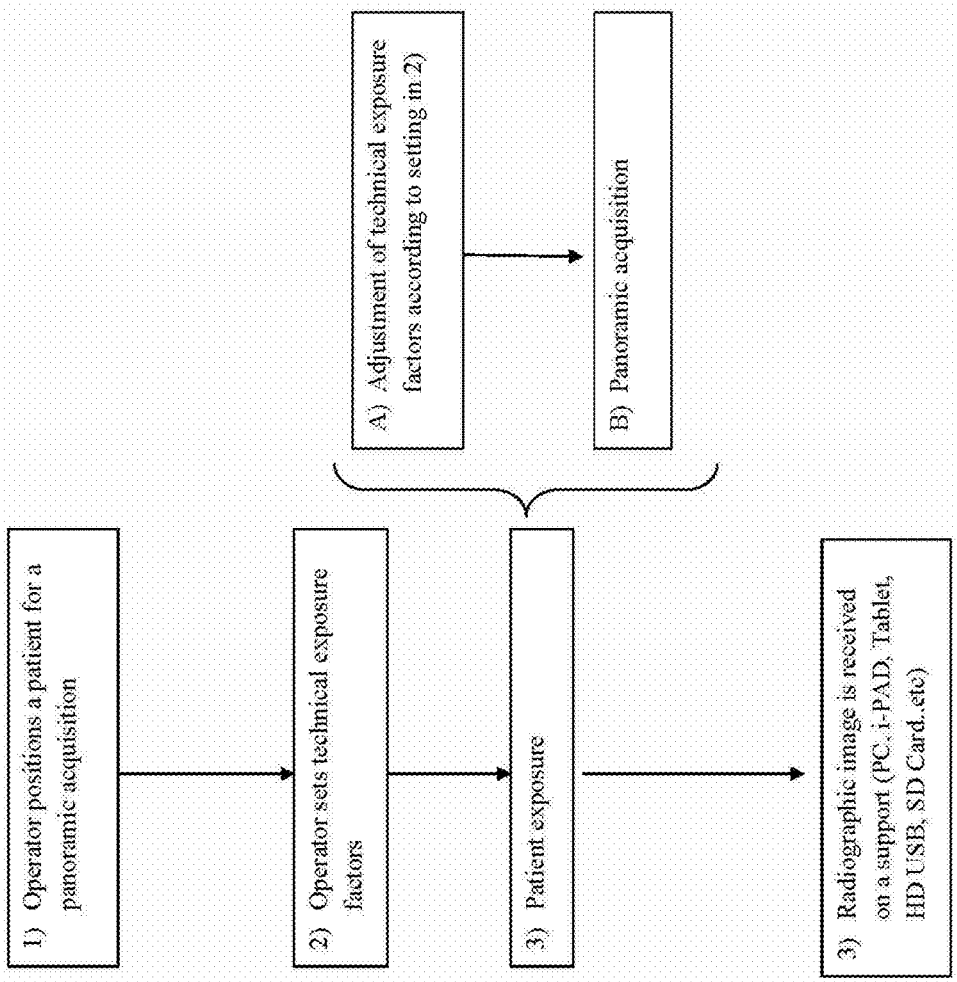
FIG. 4: Flow diagram of the known art.

In FIG. 4 the flow diagram of user operations, i.e. the material actions that the operator must perform to acquire a panoramic image, and the flow diagram of the operations performed by an apparatus in the known art, are shown.

Figure 5:
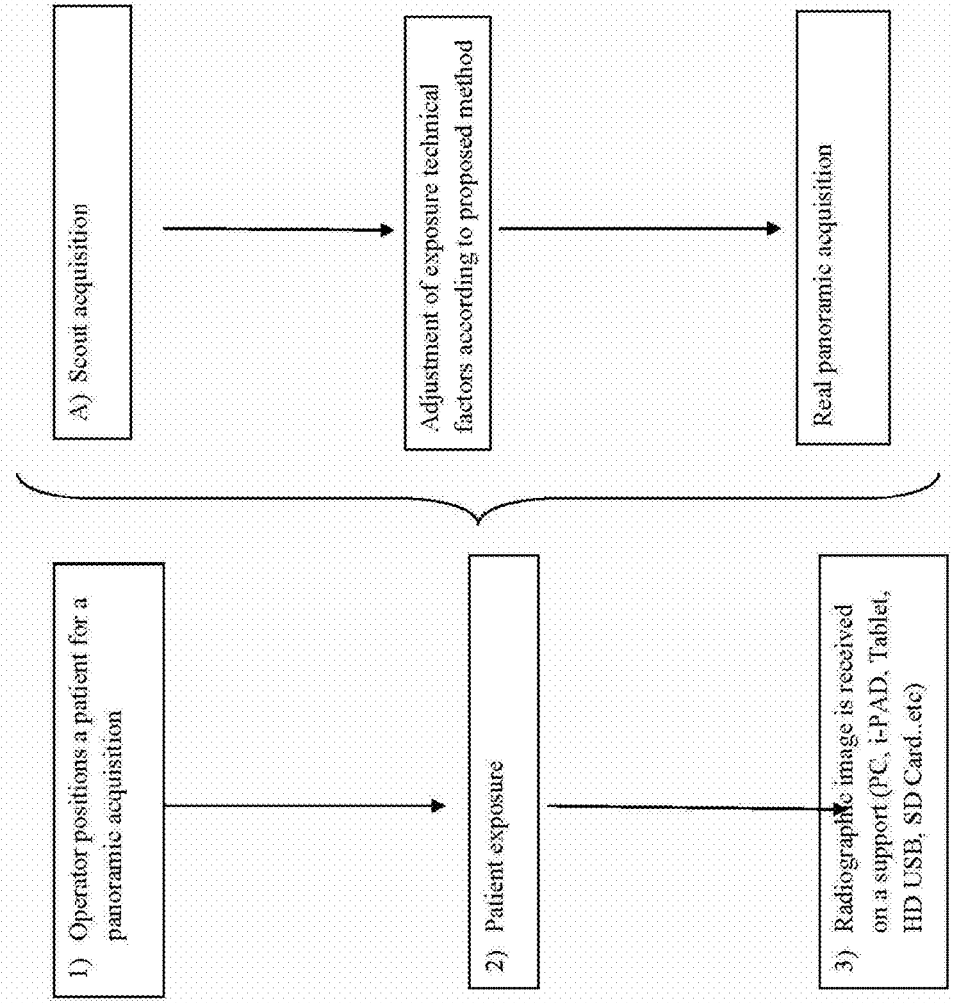
FIG. 5: Flow diagram of the present invention.
Figure 5:
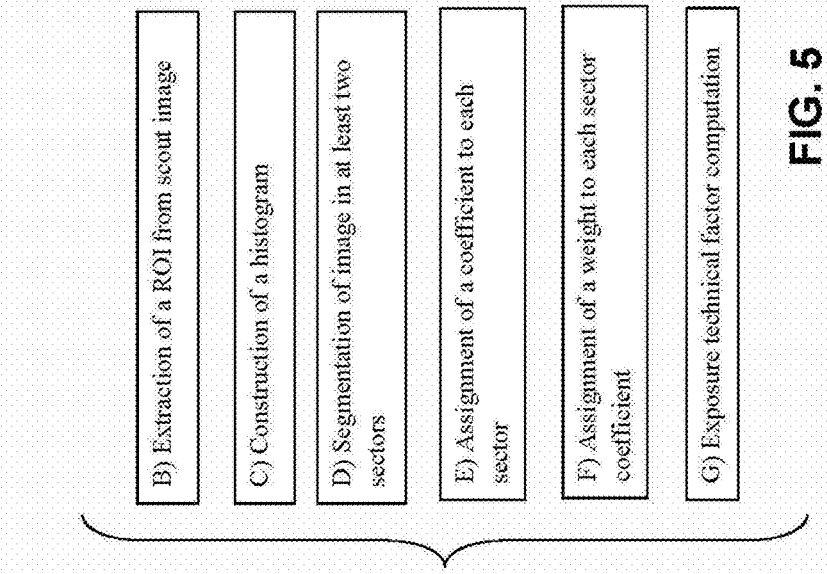

In FIG. 5 the flow diagram of user operations, the flow diagram of the operations performed by the apparatus, and the flow of the algorithm steps for computing the technical exposure factors according to the present invention are shown. Such diagram highlights, with respect to FIG. 4:

The absence of additional steps for operator/patient in the acquisition flow with respect to the known art;

The integration of the method in the operative flow of the apparatus;

The description of algorithm steps.
The method comprises the following steps:
A. Acquisition of a patient's scout image:

The positioning of the patient is the standard positioning for a panoramic acquisition, so that the patient remains in the same position even during the real acquisition (meaning the acquisition of the panoramic image).

B. Extraction of a region of interest (ROI) from the scout image.

C. Construction of a histogram of grey levels of image pixels, similar to that of FIG. 2.

D. Segmentation of the image according to a number of sectors:

In the preferred embodiment shown in FIG. 3, the number of sectors corresponds to five pre-set kinds of tissue, see above. Performing a segmentation according to different criteria is nonetheless possible. For example, the histogram can be cut only for the values that are typical for metal, in order to study this portion of the image. Alternatively, it is possible to detect the outline of the tissues having a very different radio opacity, thereby identifying the sectors of the histogram where a high gradient of grey levels is present.

E. Assignment of a coefficient to each sector:

The coefficient is a number representative of its sector. The value of such coefficient can be pre-set or depend on the information present in scout acquisition. In the present case, referring to the histogram of FIG. 3, the coefficient of metal portion is a number given by the average of the values belonging to metal sector, and hard bone is the average of the values of hard bone sector; the same applies to the other sectors.

Example: $K_i$=arithmetic average of grey levels of the pixels belonging to each sector of interest. The values computed for each sector are:

K1: 400; K2: 2150; K3:5300; K4:8600; K5:15150.

F. Assignment of a weight to each coefficient:

The weight can be assigned to the coefficient by a human operator before performing the scout acquisition, or at the installation of the apparatus, according to diagnostic needs. In the preferred embodiment, the coefficient weight is pre-set by the manufacturer, based on the fact that the kinds of tissue which can be found in a panoramic image are known. Always referring to FIG. 3 as a histogram example, we can set: W1=W5=0, because optimizing the exposure for metal or airways is useless. Typically, in a panoramic image hard bone is important, but not overexposing other tissues is also important.

In the preferred embodiment, the definition of weights is based on how many pixels belong to each kind of tissue in the entire scout image, assuming that the scout acquisition is a representative sample of the group of tissues to be evaluated.

In the example of FIG. 3, sectors 2, 3, 4 corresponding to hard bone, spongy bone and soft tissues will be considered only. For each sector weights W2, W3, W4 are computed, to be assigned to coefficient K2, K3, K4, comparing the number of pixels belonging to each sector and the total number of scout pixels.

For instance:

$Wi=Num(Segi)/Num(totROI)$;

NB: Num(A)=number of pixels ∈A; totROI is the overall number of ROI (Region of Interest) pixels;

W2=0.45, W3=0.3. W4=0.25.

Nothing prevents assigning weights according to other criteria, even independent from ROI informative content, but e.g. based on statistical or clinical elements (for edentulous patients assigning a higher weight to soft tissues might be advantageous, so as to make gum line more apparent).

G. Computation of technical exposure factors of the real acquisition:

The computing of real exposure is a result of a function of product $K_i*W_i$ of each sector, i.e. mathematically:

[kV, mA, sec, filmspeed]=$f$(K1*W1, K2*W2, K3*W3, K4*W4, K5*W5).

In the preferred embodiment, only kV are modulated with a weighted average of coefficients according to their weight. Defining more complex functions modifying the other technical exposure factors is nonetheless possible (mA, sec):

$$f(x) = \begin{cases} mA = 5 & \text{(fixed)} \\ sec = 9 & \text{(fixed)} \\ filmspeed = 10000 & \text{(fixed)} \\ kV = (a*K2*W2 + b*K3*W3 + \\ c*K4*W4)/(K2*W2 + K3*W3 + \\ K4*W4) = 74.7 \text{ kV} \end{cases}$$

In the example of FIG. 3, a, b, c are values of kV suitably chosen based on the tissue to be irradiated. In a typical X ray tube in a panoramic apparatus, the value of kV can vary in a range of 60-80 kV.

The creation of the ROI histogram is a non-onerous operation, in that finishing the scout acquisition is not necessary to perform the extraction itself. The extraction can, as a matter of fact, occur while the sensor pixels are read. The method is based essentially on simple arithmetic calculations, which can be performed by the electronic system of the apparatus in the time interval between the end of scout acquisition and the beginning of the real panoramic acquisition, without the need of big memories or computing power, beyond those anyway necessary for the normal managing of panoramic images.

It is apparent that the present method of adjustment of technical exposure factors can be usefully employed in any kind of radiologic apparatus.

Figure 6:
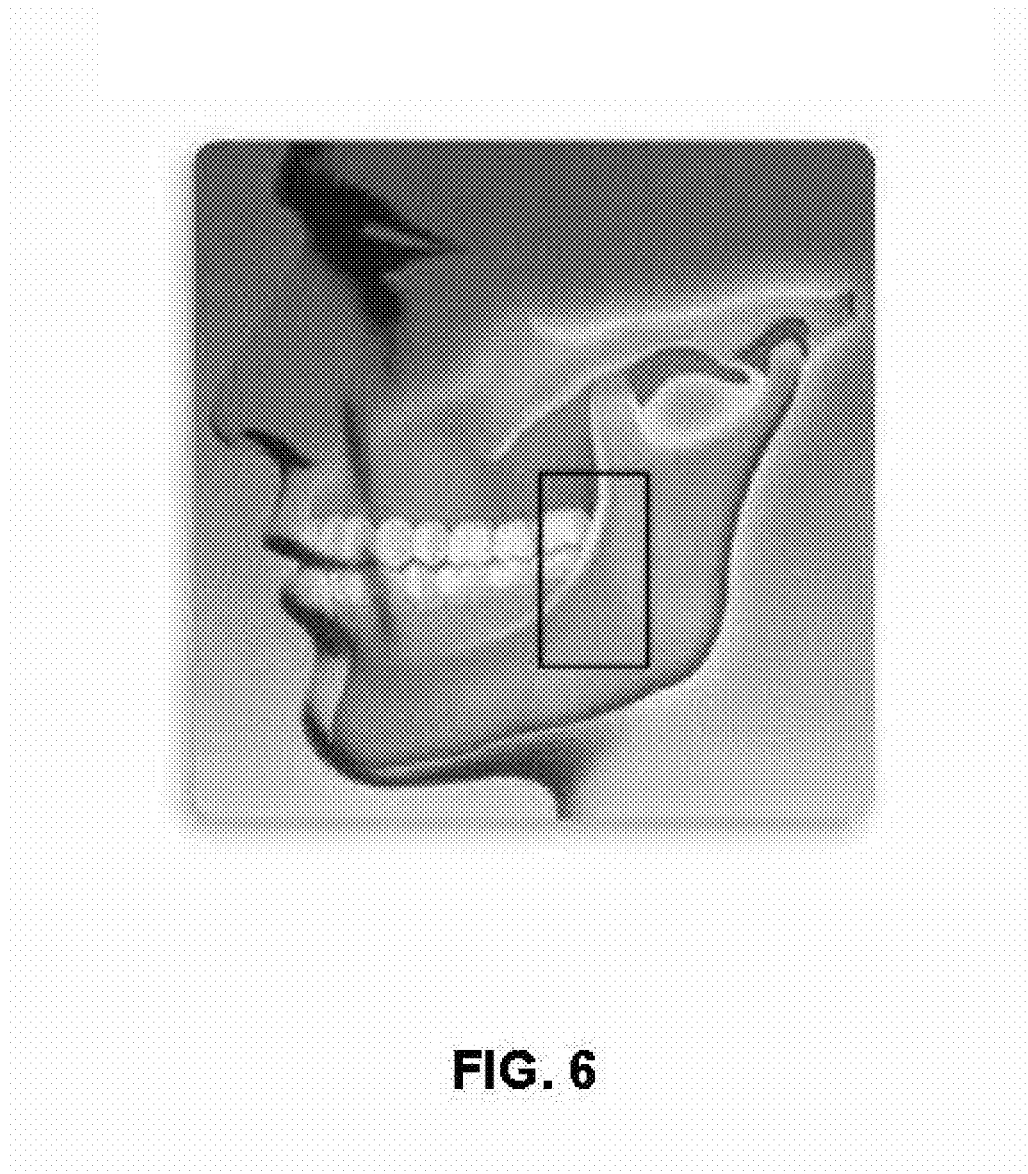
FIG. 6: Anatomic area for performing a scout acquisition.

The preferred embodiment, as said above, relates to a panoramic radiographic apparatus. In this specific case, the area where the scout image is acquired is very important. The best results were obtained by acquiring the scout image in the area highlighted by the square in FIG. 6: an area comprising a portion of the ascending ramus of the mandible, including as well distal molars (seventh, eighth teeth), comprising as well a portion of the maxilla. In this way the three kinds of tissue (hard bone, spongy bone and soft tissues) are present in the scout and, as a consequence, in the histogram, and therefore differentiating the histogram in the three meaningful sectors for the calculation of technical exposure factors is possible.

An important advantage of the present invention is that the calculation and the consequent adjustment of technical exposure factors occur completely automatically, without any action by the operator, who must only suitably position the patient in the positioning device.

With regard to scout acquisition, some clarifications are needed. The scout exposes a limited portion of the patient. Supposing that the time necessary for acquiring the patient's whole dental arch is 100, the scout is performed exposing the patient for a time range of 1-8. All this occurs with the same technical exposure factors, therefore, the X-ray dose administered to the patient for the scout is a small fraction of the total administered dose. This dose increase is justified because the total dose is then tailored on that specific patient, with a suitable cost/benefit ratio, in addition to preventing the risk of re-takes. In this way an X-ray dose with the technical exposure factors typical of the acquisition of real panoramic images is administered for a limited time. This is advantageous also for the entire acquisition time, which is only slightly prolonged.

In an alternative embodiment, administering an equivalent X-ray dose using a reduced current for a more prolonged time is possible, with equal X-ray dose.

In the preferred embodiment, scout acquisition can be considered as a fraction of the acquisition of the real panoramic image under every point of view: patient positioning, X-ray dose, time. It is nonetheless possible acquiring a scout image with a specific collimation and trajectory.

Because ROI extraction occurs at the same time as scout acquisition, and scout acquisition covers a small portion (1-8%) of the time of real panoramic acquisition, the acquisition of the real panoramic image is prolonged of a very small fraction of time. Moreover, the acquisition occurs by positioning the patient in panoramic apparatus 1 through positioning devices 6, while scout and real panoramic acquisition occur one immediately after the other. This makes the acquisition comfortable both for patient and operator.

A further aspect of the present invention, which might be provided separately or in combination with the above described features in relation to the embodiment of FIGS. 1 to 6, is described in FIGS. 7 to 12.

In the present description, the words detector or sensor are equivalent, meaning a unit receiving the radiation transmitted through the patient, and transforming the intensity of said radiation into electric signals corresponding to the intensity of said radiation. The mechanical system 5 is provided with at least two, possibly three, different degrees of freedom of movement, which allow the rotation of C-arm 4 around an axis R perpendicular to the longitudinal extension of the arm, and intermediate between X-ray source 2 and detector 3, and the translation of said axis of rotation R according to at least one, possibly two, different directions X, Y in a plane perpendicular to said axis of rotation R of C-arm 4.

Generally, in present day digital panoramic apparatuses, before exposure, the rotating group, consisting of C-arm 4 and X-ray source 2 and detector 3, is positioned in the so-called angular "patient entry" position, i.e. the position wherein, according to the mechanical structure of the apparatus, patient entry into the compartment below the arm between X-ray source and detector, and the access into patient positioning device 6, are allowed.

In the present exemplary embodiment, this position is reached by positioning C-arm 4 with its longitudinal axis perpendicular to patient positioning device 6, i.e. to the anteroposterior axis of patient's skull positioned in said patient positioning device 6, in order to allow a comfortable access of the patient to the positioning device.

From this position, which can be called RESET, C-arm 4 must move to "EXAM START" position, i.e. to the point wherein X-ray emission starts, with the consequent acquisition of patient radiographic image. In most exams these two positions (RESET and EXAM START) do not coincide.

In a panoramic acquisition, in particular, image acquisition and therefore exposure starts while the rotating arm 4 is positioned so that X-ray sensor 3 is behind the patient's condyle, and the X-ray tube, i.e. X-ray generator 2, is angularly displaced of about 30°-55° with respect to RESET position.

For good ergonomics, the scout acquisition should be performed so that the trajectory of rotating arm 4 during scout acquisition starts from RESET point and ends in the EXAM START position.

FIG. 7 shows in a very stylized way X-ray source 2 and digital bi-dimensional X-ray detector 3 united by C-arm 4; the system rotates around patient 11.

Figure 7A:
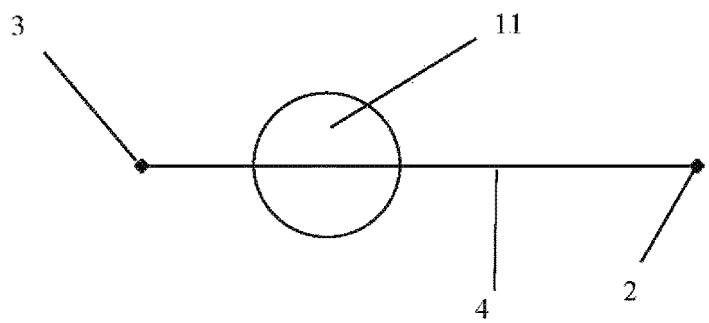

FIG. 7A shows the typical RESET position. From here the assembly X-ray source 2, detector 3 and C-arm 4 of apparatus 11 must go to the position EXAM START shown in FIG. 7C, passing through the position shown in FIG. 7B.

Figure 7B:
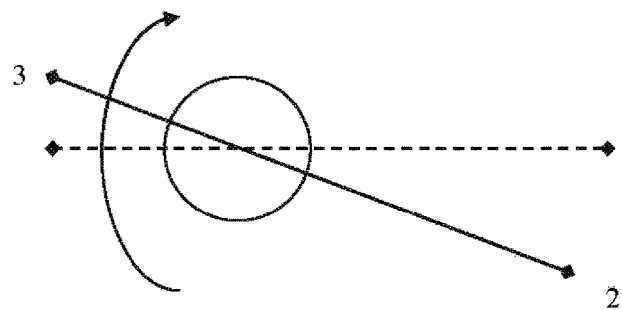
Figure 7C:
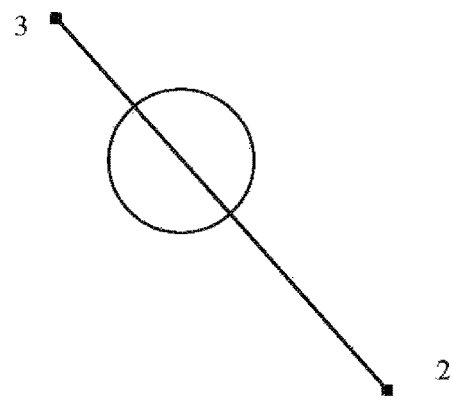

In FIG. 7B, the sense of rotation of C-arm 4 is clockwise, as shown by the curved arrow. C-arm 4 rotates angularly displacing X-ray source 2 and detector 3 around patient 11 to bring the C-arm 4 and said X-ray source 2 and detector 3 from the position as in FIG. 7A to the position as in FIG. 7C. A key feature of the invention relates to exploiting the movement shown in FIG. 8B to acquire a scout image.

Figure 7D:
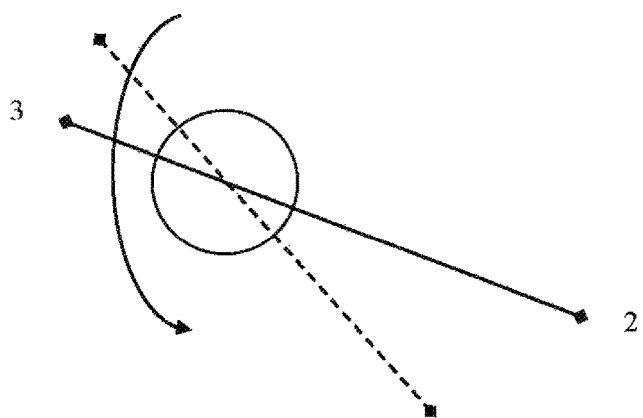

FIG. 7D shows the acquisition of the real panoramic image, performed in a direction opposed to that of the scout acquisition. In the present embodiment, the real acquisition is performed anti-clockwise, as shown by the curved arrow. In FIG. 7B the dotted line indicates the position of C-arm 4 in RESET position, and therefore allows visualizing the movement that C-arm 4 has performed during scout acquisition. In FIG. 7D the dotted line indicates the position of C-arm 4 at exam start, and allows therefore visualizing the movement that C-arm 4 performs during the acquisition of the real panoramic image.

Any type of bi-dimensional digital detector can be represented as an ordered set of columns, each formed by X-ray photosensitive elements.

The two main acquisition technologies known in the art are:

Full-frame systems, typical, but not exclusive, of C-MOS detectors. In full-frame systems, all detector columns are exposed at the same time, and at pre-set periods of time are read all together, according to a given order. Once they have been read, their information content is cancelled. The final image is obtained reconstructing the information read in each frame;

Time-Delay Integration (TDI), typical, but not exclusive, of CCD detectors. In TDI systems all detector columns are exposed at the same time, and at pre-set period of times only one of the two columns at the ends of the detector is read, which is called read-out column. The information content of all non-read columns is shifted to the adjacent column on the right or on the left, depending on detector setting, summing it up to information content already present in that column. In this way, detector columns, during the shifting between the first position and read-out position, gather information content minimizing the quantity of X-ray dose administered to patient. The final image is obtained reconstructing the information read in each column.

The following description relates to two different embodiments, each using a different bi-dimensional digital detector, C-MOS and CCD, the implementation of which poses different challenges.

The first embodiment makes use of full-frame technology, coupled with a C-MOS detector. Although this methodology of acquisition is more onerous under the point of view of both hardware and final image reconstruction, it does not pose limitations neither in the read-out direction of columns, and therefore nor in the rotation direction of the system around patient.

Figure 8A:
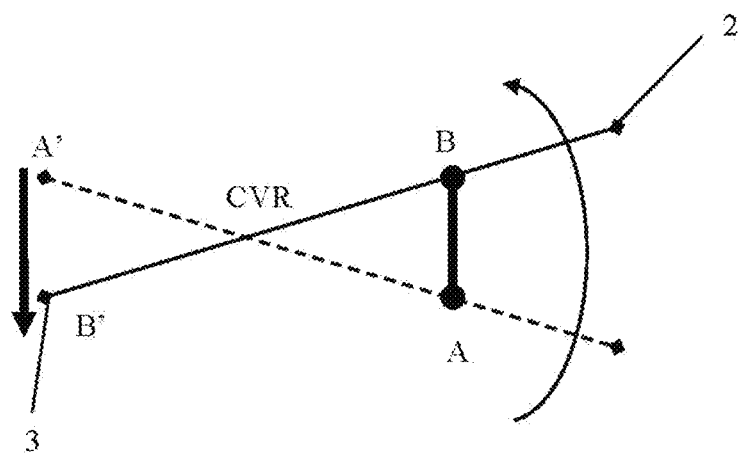

In FIG. 8A a small portion of an acquisition is shown. As known, a panoramic is formed by successive acquisitions performed by the digital detector, which are then processed to provide the image of a whole patient's arch. In FIG. 8A, the dotted line indicates the starting position of C-arm 4 at time $t_0$, while the continuous line indicates the successive position of C-arm 4 at time $t_1$. Between $t_0$ and $t_1$ the acquisition of a small anatomic portion occurs, represented by segment AB, which is projected on sensor 3 in the positions A' and B', respectively.

The curved arrow indicates the rotation direction of C-arm 4, while the bold linear arrow indicates the reading direction of detector, which must be coherent with the rotation direction of exposure.

Since C-arm 4 of the present invention has three degrees of freedom of movement, i.e. rotation around axis R and translation in the two directions X, Y, the virtual center of rotation, represented in the Figure with CVR, does not necessarily correspond to the axis of rotation R of C-arm 4, but the center of rotation R can be translated during its rotation in the plane perpendicular to rotation axis in the directions X, Y. This leads to the formation of a virtual center of rotation CVR for all or part of overall acquisition trajectory. System controlling two or more axes can generally move CVR during acquisition so as to obtain complex trajectories.

Here the term "virtual center of rotation" (CVR) has the meaning of instant center of rotation as already defined above.

Figure 8B:
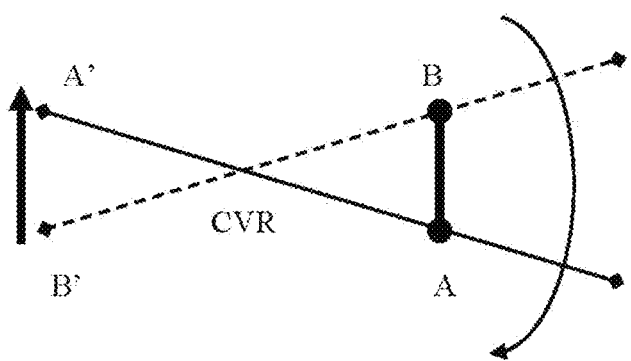

FIG. 8B shows the small portion of acquisition of FIG. 7A, wherein the direction of rotation and direction of detector reading are inverted with respect to FIG. 8A, as shown by the curved arrow.

Full-frame technology for C-MOS systems allows to read detectors indifferently in both directions, and therefore this embodiment does not have particular difficulties in its implementation.

The second embodiment makes use of TDI technology coupled with a CCD X-ray detector.

Figure 9A:
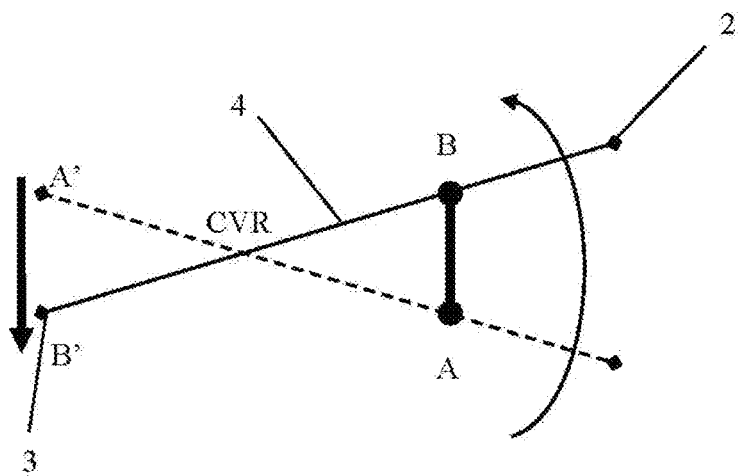
FIGS. 9A-9B: Movements of said rotating arm in a TDI acquisition system, showing in FIG. 9A that one reading direction is possible and in FIG. 9B that the opposite direction is not possible.
Figure 9B:
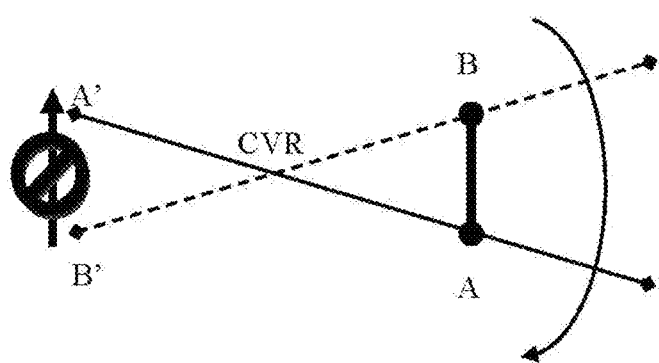

With respect to the first embodiment using a C-MOS detector, the read-out direction of a CCD detector is pre-set by the manufacturer of the detector. In order to acquire the same AB object by inverting the direction of trajectory, artifices must be used for maintaining the same read-out direction of detector, while performing the rotation for scout acquisition in the direction opposite to pre-set reading direction of detector. FIGS. 9A and 9B show that one reading direction is possible, the opposite is not.

The artifice consists in using trajectories of movement of the assembly comprising C-arm 4, X-ray source 2 and detector 3 wherein the virtual center of rotation CVR shifts with respect to the position shown in FIG. 9A. Different configurations are possible, which are shown in FIGS. 10A, 10B, 10C.

Figure 10A:
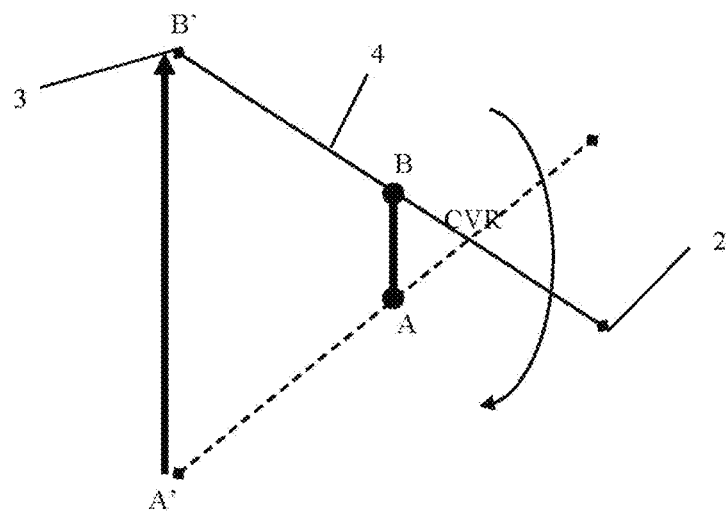
FIGS. 10A-10C: Movements of said rotating arm which are possible by shifting the virtual center of rotation. wherein in FIG. 10A the virtual center of rotation is at a first point, in FIG. 10B is at a second point, and in FIG. 10C is at a third point.

FIG. 10A shows the shifting of position of the virtual center of rotation (CVR) beyond object (AB), but in a point situated between the object and X-ray source 2.

Figure 10B:
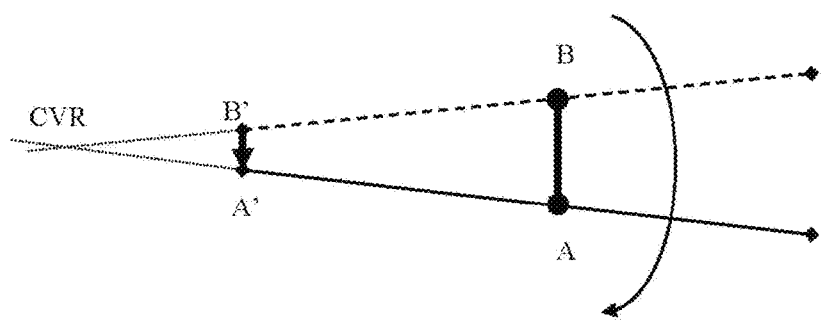

FIG. 10B shows the shifting of the position of the virtual center of rotation (CVR) beyond the detector (A'B').

Figure 10C:
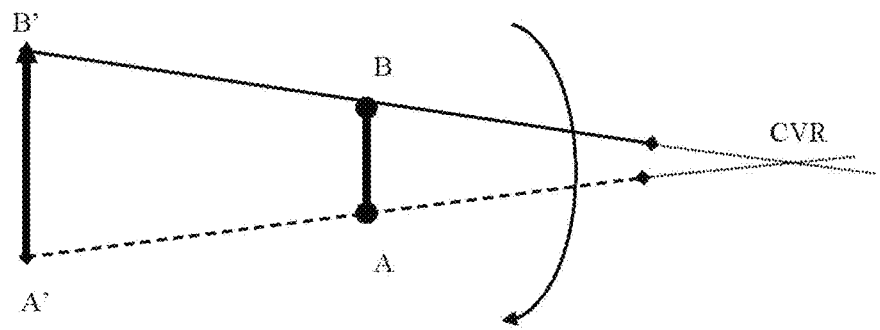

FIG. 10C shows the shifting of the position of the virtual center of rotation (CVR) beyond object (AB), out of the interval X-ray detector-source.

The configurations shown in FIG. 10A and 10C are of purely theoretical interest, in that the reading direction of detector is still "forbidden".

Instead, the configuration shown in FIG. 10B is usable in that the read-out direction of detector continues to be the in pre-set direction of the detector. Moreover, in the configuration shown in FIG. 10B, the final arm 4 position is the most compatible with the position of exam start.

Figure 11A:
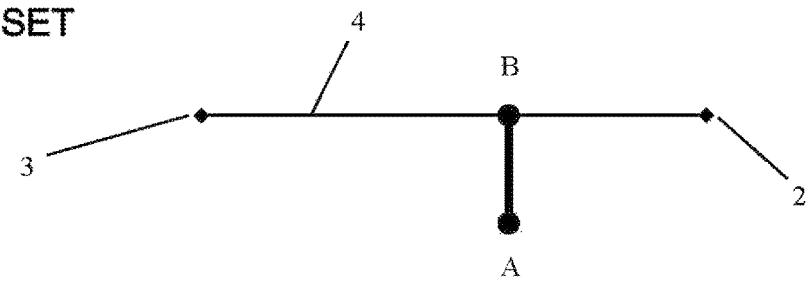
FIGS. 11A-11D: Movement steps of rotating arm during the acquisition of an overall scout+panoramic image in a TDI acquisition system according to the present invention, wherein in FIG. 11A the virtual center of rotation is at reset position, in FIG. 11B is at a first point, in FIG. 11C is at a second point, and in FIG. 11D is at a third point.

The acquisition of a whole panoramic image is shown in FIG. 11, with FIG. 11A depicting a reset position.

Figure 11B:
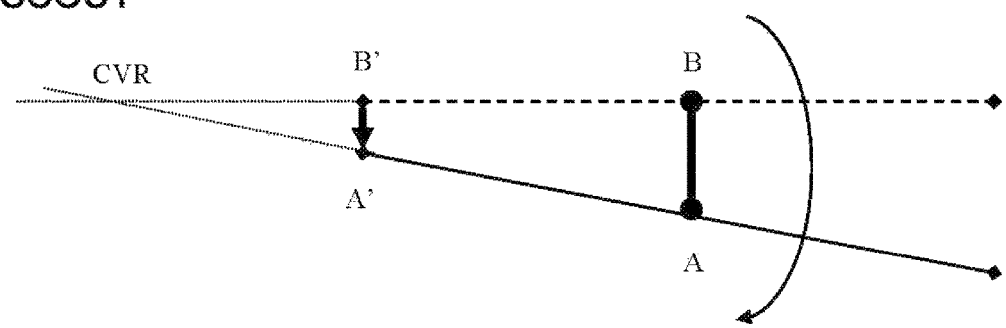
Figure 11C:
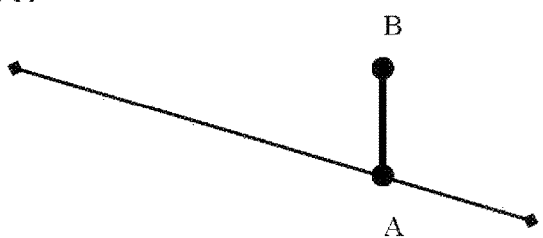
Figure 11D:
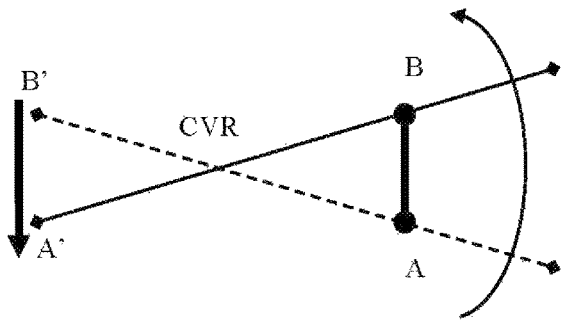

During scout acquisition a complex trajectory is performed, wherein the virtual center of rotation (as defined above) moves in the neighborhood of point CVR shown in FIG. 11B, while during the acquisition of the real panoramic image the virtual center of rotation describes a complex trajectory in the neighborhood of point CVR shown in FIG. 11D. As it is apparent in comparing FIGS. 11B and 11D, during scout acquisition CVR is beyond X-ray sensor 3, on the opposite side to X-ray source 2, while during real panoramic acquisition CVR is between the object to be acquired and X-ray sensor 3.

It is apparent that the definition of the virtual center of rotation is not free from consequences on the magnifying factor of the image, and therefore the different magnifying factors will have to be taken into account in the scout with respect to the real acquisition, or positions of CVR will have to be chosen so as to have the same magnification.

The setting of the virtual center of rotation (CVR) according to the configuration of FIG. 10B allows bringing back the acquisition of scout and real image to what is shown in FIG. 7, i.e. the direction of scout acquisition is opposed with respect to acquisition direction of real panoramic image.

Basically, FIG. 11 corresponds to FIG. 7, wherein the acquisition is partitioned in four stages $t_0$, $t_1$, $t_2$, $t_3$ and therefore the object to be acquired is not the whole dental arch indicated in FIG. 7 with 11, but the successive small anatomic portions AB acquired at each time by detector 3.

In FIG. 11 it is apparent that each final point of C-arm 4 in a given step, which in the figures is indicated with dotted line, corresponds to the starting point of the successive step. As a consequence, all the steps (RESET, SCOUT, EXAM START and EXAM) can be performed one after the other, minimizing the acquisition time of the whole panoramic image, formed by scout plus real acquisition.

The present description always referred to the preferred embodiment, for the acquisition of a panoramic image of a patient; it is however apparent to the skilled person that this method for acquiring a scout before the acquisition of a real panoramic image can be advantageously used also for acquisitions according to different trajectories, e.g. performing acquisitions on condyles, maxillary sinuses, small arch portions.

Moreover, the same method can be used in cone beam apparatuses for the acquisition of volumetric three-dimensional images (Cone-Beam Computerized Tomography, CBCT).

The invention claimed is:

1. A method of patient specific, real time automatic adjustment of a technical exposure factor selected from the group consisting of X-ray tube power (kV), X-ray tube current (mA), exposure duration (sec), and film speed to acquire a radiographic image, the method comprising the following steps:
   (a) performing a scout acquisition of an image of a specific anatomical area of a patient within a larger area to be examined using pre-defined parameters;
   (b) extracting a region of interest (ROI) from the scout acquisition, said region of interest being selected as having at least two kinds of tissue selected from the group consisting of hard bone, spongy bone, and soft tissue;
   (c) developing a grey level histogram of image pixels from the ROI;
   (d) segmenting the grey level histogram into a plurality of pre-set sectors, each of the pre-set sector being differentiated in relation to the at least two kinds of tissue;
   (e) assigning a coefficient to each sector, said coefficient being calculated as an arithmetic average of pixel values in one sector;
   (f) assigning a weight to each coefficient, said weight being calculated as a function of a number of the image pixels in each sector of the grey level histogram in relation to a total number of the image pixels in the histogram or in the ROI;
   (g) computing an exposure parameter as a function of the coefficient and the corresponding weight assigned to each sector; and
   (h) performing an exposure of a real acquisition using the exposure parameters.

2. The method according to claim 1, wherein the step of performing a scout acquisition is performed in a fraction of time in a range of 1-8% with respect to a total time of the real acquisition.

3. The method according to claim 2, wherein said scout acquisition is performed using same values of X-ray tube power and film speed as the real acquisition for a limited time with respect to the real acquisition, using a higher current value.

4. The method according to claim 1, wherein the step of assigning a coefficient comprises assigning a coefficient that is a function of average and standard deviation of pixels grey levels.

5. The method according to claim 1, wherein the step of assigning a coefficient comprises, for some sectors not having a clinical interest, assigning a coefficient that is equal to zero.

6. The method according to claim 1, wherein the step of assigning a weight comprises assigning a weight according to clinical importance of tissue represented by the coefficient or to a kind of examination to be performed.

7. The method according to claim 1, wherein the real acquisition is an acquisition of a panoramic dental image.

8. The method according to claim 7, wherein the technical exposure factor is only the X-ray tube power.

9. An apparatus (1) for acquiring radiographic images comprising:

an X-ray source (2) projecting a collimated X-ray bundle across a patient (11);

a bi-dimensional X-ray detector (3) positioned to measure intensity of radiation after said X-ray bundle has crossed the patient;

a C-arm (4) on which the X-ray source (2) and the bi-dimensional X-ray detector (3) are fixed, the C-arm (4) being provided with at least two movements, a first movement being a rotational movement around an axis of rotation (R), and a second movement being a translational movement of the axis of rotation (R) along a first direction of translation (Y) in a horizontal plane perpendicular to the axis of rotation (R) or another rotational movement of the axis of rotation (R) of the C-arm (4) around a second axis of rotation, wherein a position of the C-arm (4) is adjustable according a height of the patient along a mobile post (7);

a mechanical system (5) configured to enable the rotational movement and the translational movement of the C-arm around the patient, so as to acquire radiographic images from different positions;

a device for positioning the patient; and an electronic system controlling and synchronizing operation of apparatus components, wherein the apparatus is configured to perform the following steps:

performing a scout acquisition of an image of a specific anatomical area of a patient within a larger area to be examined using pre-defined parameters;

extracting a region of interest (ROI) from the scout acquisition, said region of interest being selected as having at least two kinds of tissue selected from the group consisting of hard bone, spongy bone, and soft tissue;

developing a grey level histogram of image pixels from the ROI, segmenting the grey level histogram into a plurality of pre-set sectors, each of the pre-set sector being differentiated in relation to the at least two kinds of tissue;

assigning a coefficient to each sector, said coefficient being calculated as an arithmetic average of pixel values in one sector;

assigning a weight to each coefficient, said weight being calculated as a function of a number of the image pixels in each sector of the grey level histogram in relation to a total number of the image pixels in the histogram or in the ROI;

computing an exposure parameter as a function of the coefficient and the corresponding weight assigned to each sector; and performing an exposure of a real acquisition using the exposure parameters.

10. The apparatus according to claim 9, further comprising a movement system providing a translational movement of the axis of rotation (R) of the C-arm (4) along a second direction of translation (X) in the horizontal plane perpendicular to the axis of rotation (R) of the C-arm (4), the second direction being different from the first direction of translation (Y), or a mechanism configured to translate the axis of rotation (R) of the C-arm (4) according to a rotational movement around another axis of rotation parallel to axis of rotation (R).

11. The apparatus according to claim 9, wherein the apparatus (1) is configured to perform a method of patient specific, real time automatic adjustment of a technical exposure factor selected from the group consisting of X-ray tube power (kV), X-ray tube current (mA), exposure duration (sec), and film speed to acquire a radiographic image.

12. The method according to claim 1, wherein the specific anatomical area comprises an ascending ramus of a mandible having distal molars and a portion of a maxilla.

* * * * *